(12) United States Patent
Thomas

(10) Patent No.: US 6,913,935 B1
(45) Date of Patent: Jul. 5, 2005

(54) MULTIPLE ASSAY METHOD

(75) Inventor: Nicholas Thomas, Cardiff (GB)

(73) Assignee: Amersham Biosciences UK Limited, Cardiff (GB)

( * ) Notice: Subject to any disclaimer, the term of this patent is extended or adjusted under 35 U.S.C. 154(b) by 0 days.

(21) Appl. No.: 09/555,102

(22) PCT Filed: Dec. 3, 1998

(86) PCT No.: PCT/GB98/03727

§ 371 (c)(1), (2), (4) Date: Jul. 17, 2000

(87) PCT Pub. No.: WO99/64867

PCT Pub. Date: Dec. 16, 1999

(30) Foreign Application Priority Data

Jun. 10, 1998 (EP) .............................. 97309784

(51) Int. Cl.⁷ .................. G01N 33/543; C12Q 1/00
(52) U.S. Cl. ................... 436/518; 436/501; 436/517; 436/518; 436/523; 436/524; 436/528; 436/537; 436/63; 436/164; 436/172; 436/174; 436/180; 435/6; 435/7.1; 435/7.2; 435/7.72; 435/7.91; 435/7.92; 435/7.93; 435/7.94; 435/7.95; 435/287.2; 435/288.4; 435/969
(58) Field of Search ............... 435/4, 6, 7.1, 7.2, 435/7.7, 7.71, 7.72, 7.91, 7.92–7.95, 287.2, 288.4, 810, 939, 973, 975; 436/501, 516, 517, 518, 519, 520, 523, 524, 527, 528, 529–537, 63, 94, 164, 172, 174, 180, 182, 805, 806, 808

(56) References Cited

U.S. PATENT DOCUMENTS

| | | | | |
|---|---|---|---|---|
| 5,567,627 A | * | 10/1996 | Lehnen ........................ | 436/518 |
| 5,641,634 A | * | 6/1997 | Mandecki .................... | 436/501 |
| 5,723,218 A | * | 3/1998 | Haugland .................... | 428/402 |
| 5,981,180 A | * | 11/1999 | Chandler et al. ............... | 435/6 |
| 6,165,717 A | * | 12/2000 | Dower et al. .................. | 435/6 |
| 6,210,900 B1 | * | 4/2001 | Yamashita et al. ........... | 435/7.1 |
| 6,280,618 B2 | * | 8/2001 | Watkins et al. ............. | 210/222 |
| 6,287,766 B1 | * | 9/2001 | Nolan et al. .................... | 435/6 |

\* cited by examiner

*Primary Examiner*—Long V. Le
*Assistant Examiner*—Gailene R. Gabel
(74) *Attorney, Agent, or Firm*—Stephen G. Ryan; Royal N. Ronning, Jr.; Yonggong J.

(57) ABSTRACT

A method for the assay of N samples each containing a compound to be tested, comprises providing N reaction vessels each containing a population of carrier beads and other reagents for performing the assay, where N is at least 2 e.g. 80–4000. Each population of carrier beads is distinguishable from every other population. After adding the samples to the reaction vessels and performing the assays, the contents of all the reaction vessels are mixed and subjected to analysis by flow cytometry. By means of flow cytometry, each carrier bead is rapidly analysed to identify its population and also to determine the presence or concentration or biological activity of the compound to be tested.

14 Claims, 3 Drawing Sheets

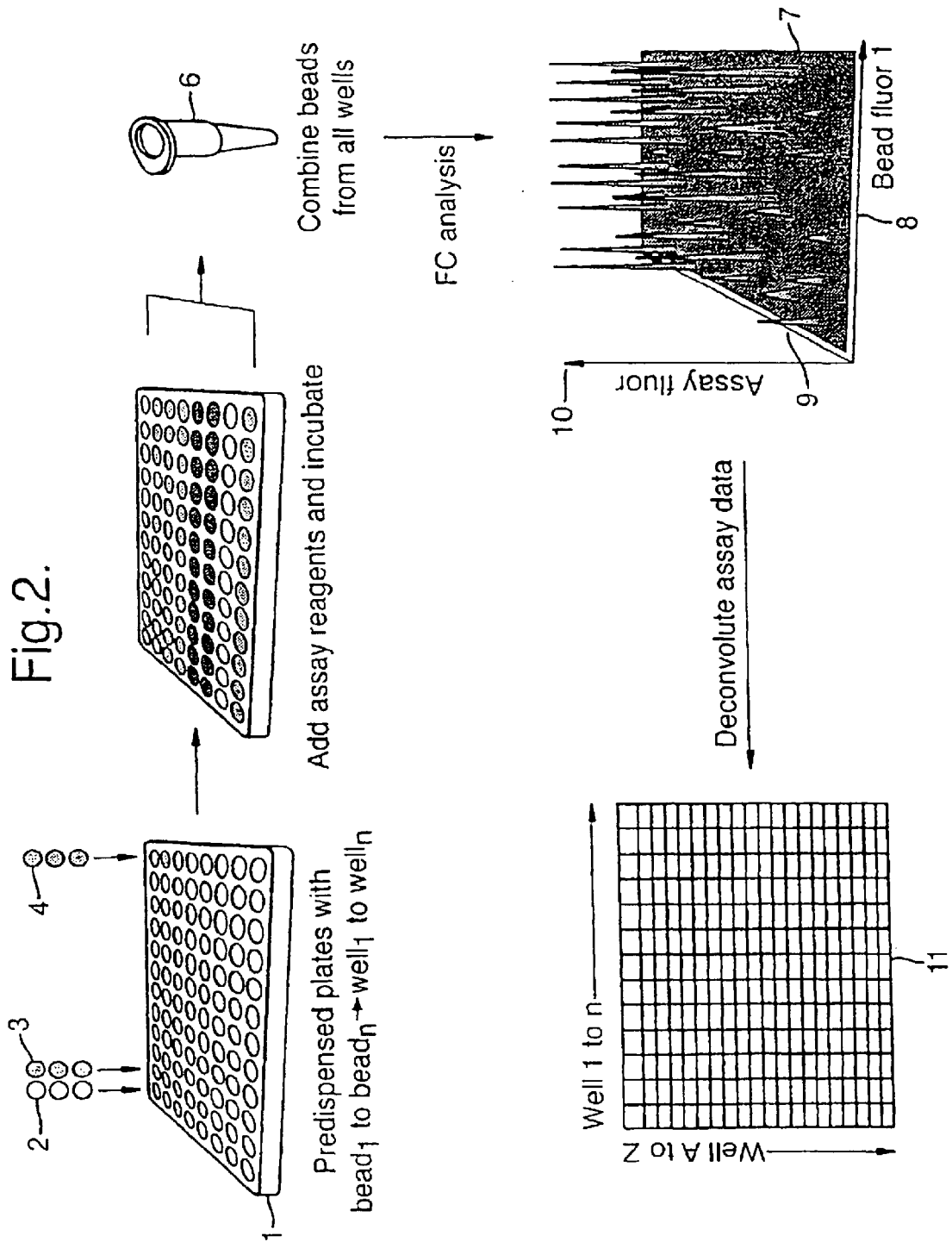

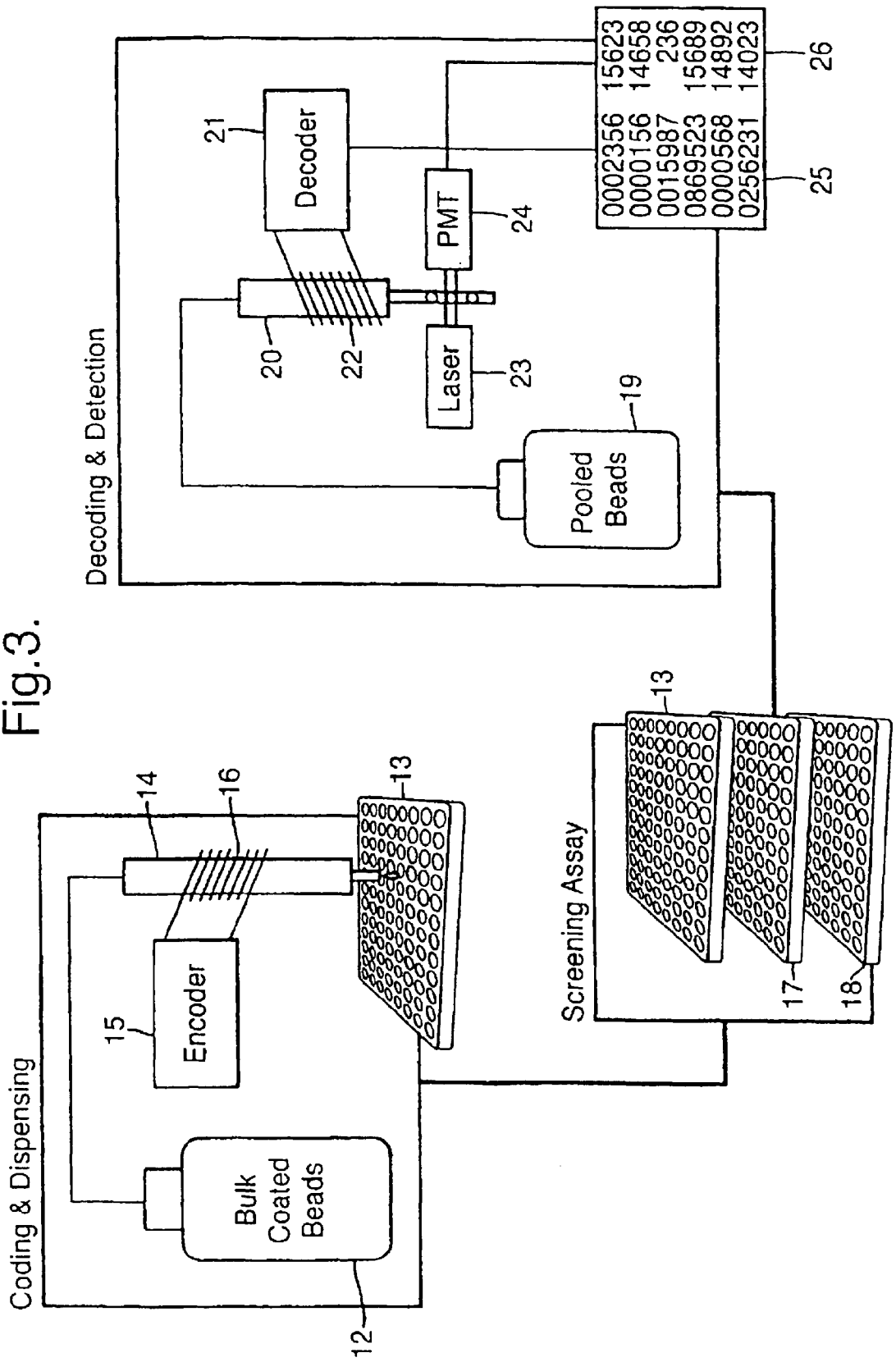

MULTIPLE ASSAY METHOD

This nonprovisional application is a 371 national stage entry of international Application Number PCT/GB98/03727 which has a filling date of Dec. 3, 1998, now published as international Publication Number WO 99/64867.

This invention relates to a multiple assay method suitable for performing high-throughput screening for drug discovery and specifically to a procedure which provides for large-scale parallel processing and analysis of results from many thousands of separate biological assays.

BACKGROUND OF THE INVENTION

1. Field of the Invention

The process of high-throughput screening (HTS) is central to the objectives of the pharmaceutical industry, i.e. to discover, develop and market new drugs (Lutz et al, (1996) Drug Discovery Today, 1(7), 277–86). In the HTS process, drug candidates are screened for possible effects in biological systems. Increasingly, there is a drive to test larger numbers of compounds in each screen, and screening assays examining 100,000 compounds or more are typical. This requires highly sophisticated robotic automation and instrumentation to achieve efficient levels of throughput. In general, modem screening techniques utilise multiwell plate technologies to allow transfer of the many thousands of assays between the various stages in the procedure. Such plates may contain between 96 and 1536 or more individual wells, where each well contains the same reagents as all other wells in the screen, except for the individual compounds under test which are each present in only one well. The standard format and layout of the multiwell plates allows fast robotic handling and liquid dispensing devices to be used to maximise throughput.

2. Description of Related Art

In many HTS applications the rate limiting step occurs in assay analysis at the stage of detecting and measuring the signal from the label used in the assay. This step is a serial process, each well of the multiwell plate being measured in turn. Such measurements typically require from one to several seconds to perform, with the consequence that the time taken to analyse a multiwell plate can be considerable.

Flow Cytometry (Parks, D. R. and Herzenberg, L. A. 1984, Methods in Enzymology 108, 197–241) is a technique for analysing cells or particles according to their size and fluorescence. The cells or particles are carried by a thin rapidly moving stream of liquid which is transected by light beam(s) from one or more lasers or other light sources. Photo-detectors register light-scattering and fluorescence arising from a cell or particle passing through a light beam and the resulting electronic signals are processed to yield analytical data. In contrast to the slow data acquisition time of multiwell plate readers, instrumentation for flow cytometry enables very rapid analysis of many thousands or millions of cells or other particles in a high speed stream of liquid and is typified by very fast measurement times, for example of the order of 1 $\mu$sec/event.

Flow cytometry has other characteristics which make it favourable for analysis in HTS. Firstly, the very small analysis volumes required are compatible with the current trend to scale down assays as a means of increasing throughput. Secondly, flow cytometry is inherently an homogeneous measurement system, i.e. measurement of the fraction of a specific fluorescent dye-labelled ligand in a particular state can be accomplished without the need to physically separate that type of fluorescent dye from the total type. In HTS applications, this is a desirable property as it removes the need for washing or separation stages to isolate the desired type of label prior to measurement. Flow cytometry has been extensively used for diagnostic assays to measure a wide range of analytes in blood and other biological fluids, for example in immunotyping and measurement of cell surface antigens associated with HIV infection (Patterson, B. K. et al J. Virology, (1995) 69(7) 4316–4322). Despite its inherent advantages however, flow cytometry is disadvantaged by low throughput rates which are a consequence of serial processing. While read times are very fast, allowing many thousands of events to be analysed/second within a single assay, there is a considerable delay between samples which currently limits overall throughput to <100 separate analyses/hour.

A desire to have a higher throughput in these applications has led to the development of multiplex methods which allow more than one analyte to be measured simultaneously by flow cytometry. Multiplexing is achieved by carrying out solid phase linked assays using plastic or latex beads as assay substrates. By using a number of discrete bead types which are individually distinguishable from each other, where each bead type carries reagents for one assay, standard flow cytometer instrumentation may be used both to identify the bead type and to measure the assay signal associated with each bead, and therefore to perform several tests in parallel on a single sample, for example to measure the presence of multiple analytes in human sera (McHugh T. M., 1994, Methods in Cell Biology 42, 575–595). Discrimination between bead types can be achieved by size (Frengen J. et a/, 1995, Journal of Immunological Methods, Volume 178, p141). by colour or fluorescence (Fulwyler M. J. UK Patent 1,561,042) or by electronic means (Mandecki W. U.S. Pat. No. 5,641,634).

Multiplexing of flow cytometry assays introduces an element of parallel processing into an otherwise serial process, so that while the delay between samples remains as before, the amount of information gathered from each sample is increased several fold giving a resulting increase in data acquisition rates. This is ideal for measurement of multiple analytes in a single sample, i.e. 'one sample, many tests'. However, the requirements of high throughput screening, i.e. 'one test, many samples', are the reverse. In HTS assays it is a requirement that there must always be separation of assays to allow the effects of individual compounds within the screen to be determined. Consequently, methods previously described for multiplex diagnostic analyses by flow cytometry are not applicable to HTS assays.

BRIEF SUMMARY OF THE INVENTION

WO-A-93/02360 discloses a method and kit for contiguously detecting multiple analytes of interest in a sample comprising combining a sample with a composition comprising known proportions of multiple discrete sub populations of reagents, which bind specifically to analytes, which are linked to particulate supports e.g. microspheres and which may be detected by flow cytometry.

WO-A-97/14028 describes a method and kit for the multiplexed diagnostic and genetic analysis of enzymes, DNA fragments, antibodies etc. The invention employs a pool of bead subsets, the beads to of one subset differing in at least one distinguishing characteristic from beads of any other subset.

This invention provides. a method for the assay of N samples each containing a compound to be tested, which method comprises the steps of:

a) providing N populations of carrier beads where the carrier beads of each population are distinguishable from the carrier beads of every other population;
b) dispensing each of the N populations of labelled carrier beads into one of N different reaction vessels;
c) dispensing each of the N samples into one of the said different reaction vessels;
d) providing in each of said N different reaction vessels reagents for performing an assay whereby a signal moiety is caused to be partitioned in a compound-related manner between the carrier beads in that reaction vessel and a supernatant fluid;
e) combining the contents of all of the reaction vessels into a mixture; and
f) subjecting the mixture to analysis by flow cytometry, to assay the signal moiety associated with each of a sequence of individual beads; wherein N is greater than or equal to 2.

The invention also provides a kit for performing the assay method, which kit comprises the N populations of the carrier beads where the carrier beads of each population are distinguishable from the carrier beads of every other population, and wherein all the beads are pre-coated with the same reagent at substantially the same surface concentration for performing the assay, together with a supply of reagents for performing the assay, where N is at least 2.

Suitably, N is greater than or equal to 2; preferably in the range from 2 to 100,000, more preferably in the range from 80 to 4000.

Suitably, the carrier beads are coated with a reagent, bound thereto, the reagent optionally carrying a signal moiety.

Suitable assay formats which employ a reagent carrying signal moiety bound to the carrier bead include those which, either by chemical or by enzymatic action, involve the release of a signal moiety from the bead. In the alternative, a reagent carrying the signal moiety is added in solution in a suitable medium, and include assays which involve binding the signal moiety either covalently or non-covalently, to a reagent immobilised on the bead.

Suitably, the reaction vessels form the wells of a multiwell plate.

In step d) of the method, an assay reaction is performed in which a signal moiety is caused to be partitioned in a compound related manner between carrier beads and a supernatant fluid. Various examples can be given. In one example, an assay is performed to determine the presence or absence in each sample of a particular compound to be tested; in each reaction vessel the signal moiety is partitioned in a manner which indicates the presence or the absence of the compound in the sample dispensed in that vessel. In another example, an assay is performed to determine the concentration in each sample of a particular compound to be tested; in each reaction vessel the signal moiety is partitioned in a manner which indicates the concentration of the compound in the sample dispensed in that vessel. In another example, which is preferred, an assay is performed to determine the biological activities of a plurality of different compounds to be tested, with each sample comprising or consisting of a different compound, generally in known amount; in each reaction vessel the signal moiety is partitioned in a manner which indicates the biological activity of the compound in the sample dispensed in that reaction vessel.

Beads suitable for use in the method of the invention are those which are compatible with processing and analysis by flow cytometry and additionally are suitable for incorporating means of identification into the bead. Preferred bead types are formed from plastic or polymeric materials, including polystyrene latexes, polyacrylates, polymethylmethacrylate, polyacrylamides, polyurethane, polyvinylidene chloride and polyvinyltoluene. Polystyrene beads are particularly preferred for use in the invention. Beads may be of a mean diameter suitable for use in flow cytometric applications. A bead size suitable for use in the invention may be in the range 1–50 $\mu$m in diameter, preferably of diameter 2–20 $\mu$ m. Preferably, beads of the same size are used in the method of the invention. Optimally, beads of mean diameter 10$\mu$m are used in the method of this invention.

Detectable labels suitable for bead identification include fluorescent molecules, absorbed or incorporated into or onto the surface of the bead. As an alternative means of distinguishing and identifying bead populations, beads of one population may be of a different size compared with beads of another population. In a further alternative, bead identification may be by electronic means, such as by the inclusion into the core of the bead of a suitable electronic tag. Detectable labels such as those described above may be used either singly or in combination to create bead populations which are uniquely identifiable.

Preferably beads including fluorescent labels are used in the method of the invention. Fluorescent labelled beads suitable for use with the invention are prepared by the incorporation of different amounts of two or more different fluorescent dyes into the body of the bead such that each combination of such fluorescent dyes defines a unique bead type. The number of possible discrete assays that can be multiplexed will be limited only by the number of bead types which it is possible to discriminate in a mixture. With current flow cytometry instrumentation, this does not pose a limitation on the utility of the procedure. Typical, modern flow cytometry instruments are capable of simultaneously measuring fluorescence at four wavelengths, together with other parameters, for example light scattering, which is a measure of the size of particles under analysis. In addition, the dynamic range of fluorescence detection is high and fluorescence may be accurately measured over several orders of magnitude. It is therefore possible to devise schemes which yield a large number of individually distinguishable bead types to serve as carriers in a HTS assay according to the present invention. For example, beads may be prepared which contain three separate, spectrally distinguishable fluorescent dyes, wherein each fluorescent dye may be present in one of 8 concentration levels. Thus it is possible to create $8^3$, that is 512 spectrally distinguishable bead types. If, in addition, 3 sizes of beads are used, the total number of bead types is 3×512=1536. This number is equivalent to the number of wells in a high density multiwell plate such as are suitable for use in HTS assays. Use of fluorescent dyes in such combinations will allow all reactions in a high density plate to be combined into a single sample for analysis by flow cytometry.

Suitable fluorescent dyes useful for bead identification are dyes which have discrete excitation and emission spectra suitable for individual identification in a flow cytometer. The exact chemical nature of the fluorescent dye is not critical to the present invention. Fluorescent dyes which may be used include, but are not limited to, fluoresceins, rhodamines, cyanine dyes, coumarins, and the BODIPY groups of fluorescent dyes. Methods for electronic coding and identification of beads are disclosed in U.S. Pat. No. 5,641,634.

BRIEF DESCRIPTION OF THE FIGURES

The figures show:

FIG. 2: Schematic representation of the mix/multiplex HTS process using fluorescence bead identification.

FIG. 3: Schematic representation of the mix/multiplex HTS process using electronic bead identification.

DETAILED DESCRIPTION OF THE INVENTION

Figure 1:
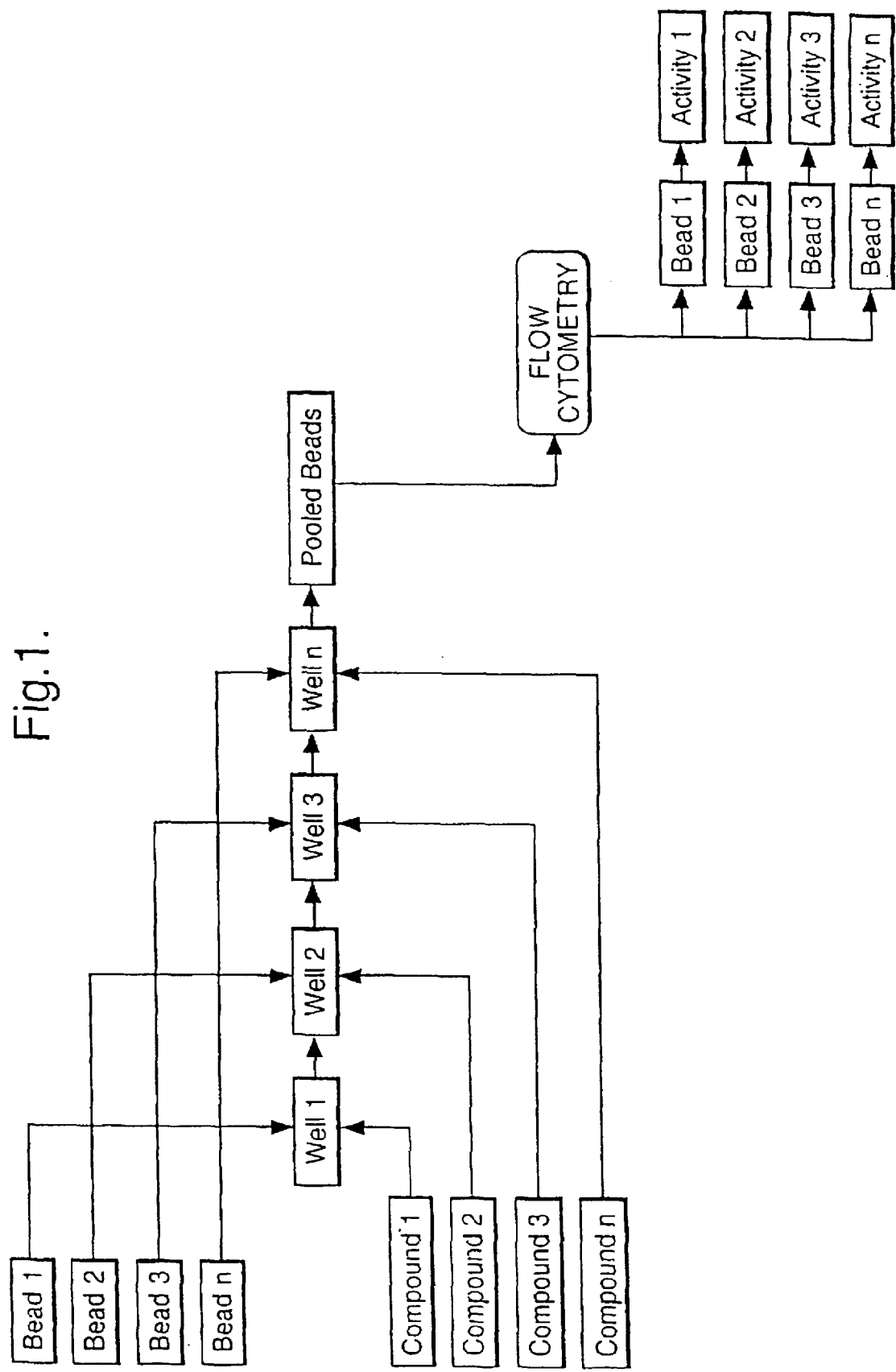
FIG. 1: Flowchart illustrating the principle of the mix/multiplex HTS process.

The above described bead types can be applied to assays commonly used in HTS applications. Such assays are conveniently categorised as one of two types.

i) The first category comprises equilibrium binding assays, in which one member of a binding pair (the reactant) is bound to the surface of the bead and samples containing compounds to be screened are tested for their effect upon the binding, (either antagonistic or agonistic) to a second member of the binding pair (the ligand), where the ligand carries a signal moiety, preferably a fluorescent label. In this way, the effect of the test sample on the binding reaction can be determined by measurement of the amount of labelled ligand bound to the bead through its interaction with its binding partner. Examples of such equilibrium binding interactions include, but are not restricted to, receptor-ligand interactions, protein-protein binding interactions and protein-DNA interactions. Irrespective of the identity of the components of the interaction, all such assays are similarly characterised by having two components where one component is bound to the bead and the second component carries a signal moiety which becomes attached to the bead through the interaction of the two components.

ii) In the second category, the assay may comprise detection and measurement of a chemical or enzymatic change in the state of an assay component bound to the bead and in which the samples containing compounds to be screened are tested for their inhibitory effects, potentiation effects, agonistic, or antagonistic effects on the reaction under investigation. Illustrative of such reactions are those which include the removal of a fluorescent dye-labelled moiety from a substrate coupled directly or indirectly to the bead through a covalent or non-covalent interaction, or alternatively, the covalent or non-covalent addition of a fluorescent dye-labelled moiety from a substrate in solution in the assay medium to a molecule coupled directly or indirectly to the bead by means of a covalent or non-covalent interaction. Examples of such assays include, but are not restricted to, the cleavage of a fluorescent dye-labelled peptide or protein by a protease, the cleavage of fluorescent dye-labelled DNA or RNA molecule by a nuclease, the joining of fluorescent dye-labelled DNA or RNA molecules to other nucleic acid molecules by ligases, the addition of a fluorescent dye-labelled nucleotide to a DNA or RNA molecule by a polymerase and transfer of a fluorescent dye-labelled chemical moiety from one molecule to another by a transferase such as acetyl transferase.

Suitable fluorescent labels for tagging ligands or substrates are those which are: a) spectrally distinct and distinguishable from any fluorescent dye used for bead identification, b) detectable by a flow cytometer and, c) capable of being attached to the ligand or substrate component of the assay by covalent or non-covalent attachment. Suitable fluorescent dyes for use in labelling ligands and substrates according to the method of the invention may be selected from the general categories of fluorescent dyes listed above. Preferably, derivatives of such fluorescent dyes having reactive or functional groups suitable for attachment to corresponding functional or reactive groups on biological target molecules are used. Examples of such reactive fluorescent dyes are sulpho-cyanine dye NHS ester derivatives as described in U.S. Pat. No. 4,268,486 (Waggoner et al). Other fluorescent reagents suitable for labelling target molecules will be well known to those skilled in the art.

Alternatively, labels useful for attachment to the ligands or substrates can be fluorescence energy transfer labels. Examples of such energy transfer fluorescent dyes are to be found in GB Pat. No. 2301833 (Waggoner et al) which relates to fluorescent energy transfer complexes containing reactive or functional groups for covalent attachment to a target. Other fluorescent energy transfer labels may be bound non-covalently to a ligand or substrate moiety, e.g. by intercalation of a dye to a dsDNA molecule. Examples of such dyes are disclosed in U.S. Pat. No. 5,401,847 (Glazer et al.

For clarity, the general principles and specific embodiments of the method according to the present invention (termed mix/multiplex HTS), are described with reference to the following figures:

With reference to FIG. 1, to perform the mix/multiplex HTS process, sufficient individual types of carrier beads are used to allow one carrier bead type for each discrete assay to be performed in a screening unit, that is one bead type for each sample to be screened. The surfaces of beads are modified, for example by coating with a binding reagent such as an antibody, protein A, streptavidin, avidin, wheat germ agglutinin or poly-l-lysine. Alternatively the bead surface may be treated by chemical modification to provide functional or reactive groups suitable for the attachment of specific assay components such as proteins, peptides, oligonucleotides, ligands and carbohydrates to the surface of the bead. Suitable functional or reactive groups include hydroxyl, amino, carbonyl, carboxyl and sulphydryl groups. Methods suitable for coupling reactants to the surface the bead are well known to those skilled in the art.

In a further illustration of the method of this invention, reference is made to two possible but non-restrictive embodiments of the process. With reference to FIG. 2, beads containing different amounts of two fluorescent dyes are used as carrier beads for the assay. To set up the assay, each type of beads (2,3,4) is added to a separate well of a multiwell screening plate (1). Pre-dispensed plates arrayed in this manner are then used as the basis for the screening process as described generally above. Once the reaction stage of the screening process is complete, a portion, or the entire contents of each of the wells in which reactions have been conducted, are mixed together into a single container (6) and analysed by flow cytometry. In the flow cytometer, two of the available fluorescence measurement channels are used to identify the bead type to which any individual bead belongs, by determining the amounts of the two fluorescent dyes present within the bead. Simultaneously, a third fluorescence channel may,be used to quantify the amount of fluorescent dye-labelled ligand or substrate bound to the surface of the bead.

In performing assays according to the method of this invention, it is convenient to refer to a screening unit which will typically correspond to assay reactions performed in one multiwell plate, where a complete screen comprises from one to many multiwell plates. Each bead type from 1–N is individually added to corresponding wells 1–N containing assay reagents, where for example in the case of a receptor based screening assay, reagents would typically comprise a receptor preparation, assay buffer and a fluorescent labelled receptor ligand. Samples containing one or more compounds to be screened are added individually to the prepared wells, samples 1–N being added to wells 1–N. In this way, a fixed correspondence is established between each sample in the screen and the bead type carrying the reactants exposed to each individual sample containing one or more compounds under test. Once the reaction stage of the assay is complete, all reactions in a screening unit are mixed together for analysis without destroying the correspondence, since on analysis by flow cytometry, both the particular bead type and the assay signal associated with it can be readily determined for any given bead in the analysed mixture. Accordingly, once analysis of the mixed samples is complete, assay signals measured from beads 1–N (activity 1–N) can be correlated with samples 1–N originally added to wells 1–N.

Display of data as an x-y-z plot (7) allows identification of individual bead types according to the relative intensities of fluorescence from bead fluorescent dyes 1 (8) and 2 (9), on the x and y axes respectively and allows intensities of assay signals for each compound in the screen to be displayed separately (10). The identity of each bead type can be determined from its x-y position and therefore the z assay signal of that type can be assigned to a single well in the original multiwell plate. Consequently all assay data from one mixed sample can be displayed as a data matrix (11) corresponding to the original layout of the multiwell plate and results examined to determine the activity of the compounds screened.

In a second possible embodiment of the process of the invention, electronic encoding is used to identify assay carrier beads. With reference to FIG. 3, in this embodiment carrier beads containing semiconductor memory devices, as described in U.S. Pat. No. 5,641,634, and coated with assay reagents particular to the type of assay being performed are used in a bulk suspension (12) as described above. The bulk beads are dispensed into multiwell plates (13) using a dispensing nozzle (14) fitted with a radio-frequency generating coil (16) controlled by encoding circuitry (15). This apparatus allows beads passing through the dispensing device to be given a unique identity through action of the radio-frequency field on the semiconductor. By this means it is possible, starting with a bulk suspension of identical beads and by moving the dispensing device from well to well, to produce a multiwell plate with an uniquely coded population of beads in each well. At this stage the screening process is continued as described above with assay reagents (17) being added to the wells of the multiwell plate, followed by samples (18) containing compounds to be screened.

For analysis, a modified flow cytometer (20) is used where the instrument is fitted with a second radio-frequency coil (22) set up to read information encoded on the semiconductor within beads through decoding circuitry (21). Pooled beads (19) passing through the instrument are first read by the decoder and secondly by the instrument's conventional fluorescence detection laser (23) and photomultiplier (24) components to give a continuous data readout of bead identity code (25) and assay fluorescence signal (26).

By the use of electronic encoding as a means of bead identification, the possible number of bead types is limited only by the capacity of the semiconductor. For example a 16 bit device would allow the characterisation of 32768 different bead types and therefore mix/multiplexing of 32768 discrete screening assay reactions. Secondly, beads may be prepared for an assay in bulk and coded directly before use, thereby removing the need to carry out preparations on each bead type individually. Radio-frequency encoding and reading removes the requirement for multiple fluorescence channels to be used for bead identification allowing either simplification of instrumentation of use of fluorescence channels to measure additional assay information.

The mix/multiplex procedure as described above allows very high throughput of individual screening assay reactions by analysis by flow cytometry in a manner which exploits the capabilities of flow cytometry instrumentation, and in particular the very fast data acquisition which can be obtained. The procedure is compatible with the wide range of different sized multiwell plates that are commonly used in HTS programs. The method of this invention is preferably used in high well density, small well volume, plates such as 1536 well plates, where the assay volume/well is 10 $\mu$l or less. The amounts of beads used in each well may be varied to accommodate the requirements of different screening assays, but will preferably be in the range 0.01–10% v/v. in respect of the assay volume, most preferably in the range 0.1–1.0% v/v. At the most preferred bead concentrations and using a preferred bead size of 10 $\mu$m, a single assay well containing 10 $\mu$l of liquid would contain a number of beads in the range 10,000–100,000 beads/well.

Each bead in any individual well is identical to every other bead in the same well and is therefore an individual assay unit which can be separately measured by flow cytometry. In performing biological assays, it is common practice to perform replicate measurements in order to take account of physical or biological variations inherent to the assay process. Such replicates typically take the form of duplicate or triplicate determinations of each assay which are carried out to obtain data typically expressed as a mean ± standard deviation, where the standard deviation is a statistical measure of the variation in the assay data which is used to assess the precision and accuracy of the data obtained. In conventional screening assays the assay comprises the whole well or tube in which the assay is performed, and therefore replication involves duplication of the entire assay. In contrast in bead based assays where each bead is an measurable unit, replicate measurements may be performed at the level of individual beads. Therefore, while an assay well may contain 10,000–100,000 beads it is not necessary in the subsequent analysis to measure every bead from that well, but only to measure sufficient beads to accumulate data which meets predetermined specifications for precision and accuracy.

The potential throughput of the process is illustrated by the following example. If a 1536 well plate is used as single screening unit, and it is determined that to obtain a statistically valid analysis it is necessary to measure assay results for 100 beads for each compound screened, the total number of beads to be analysed is 153,600. Modern flow cytometers are readily capable of performing measurements on between 1000 and 10,000 particles/second; assuming analysis at an intermediate rate of 2500 beads/second yields an analysis time of 153,600/2500=61.44 seconds or approximately 1 minute to measure the 1536 discrete assays in the multiwell plate. This compares very favourably with a time of 25.6 minutes to read results individually in a plate reader at a speed of 1 second/well. Allowing for loading of successive mixed samples on to a flow cytometer at a rate of 40/hour gives a throughput of 1536×40=61440 assays/hour or around 500,000 assays in a working day.

EXAMPLE

Streptavidin coated bead type A (yellow fluor) and bead type B (purple fluor) were pipetted into two separate wells of a microtitre plate, such that well 1 contained bead A and well 2 contained bead B. Buffer was added to well 1 and buffer containing biotin was added to well 2. Following mixing arid incubation a solution of Cy-5 labelled biotin in buffer was added to both wells. Following further incubation the contents of well 1 and well 2 were combined and the mixture analysed by flow cytometry. Measurement of Cy-5 fluorescence associated with each bead type showed high fluorescence for bead b indicating high Cy-5-biotin binding in well 1 and low Cy-5-biotin binding in well 2, correlating with the presence in well 2 of an active competitor for binding to the streptavidin on the bead surface.

What is Claimed is:

1. A method for assaying N samples, wherein N is greater than or equal to 2, said samples each containing a single compound to be tested, said method comprising:
   a) providing N populations of carrier beads wherein the carrier beads of each population comprise a detectable label for distinguishing the carrier beads of each population from the carrier beads of every other population, and
      a reactant bound thereto,
         wherein said reactant comprises a first component of a specific binding pair, and
         said reactant being the same for said carrier beads in all of said N populations;
   b) dispensing one distinguishable population of said N populations of carrier beads into a separate, corresponding one of N different reaction vessel, so that said one of N different reaction vessels contains one of said N populations, and performing said dispensing for each population of said N populations;
   c) dispensing one of said N samples having a single compound to be tested, into a separate, corresponding one of said N different reaction vessels, so that said one of N different reaction vessels contains one of said N samples and one of said N populations, and performing said dispensing for each sample of said N samples;
   d) providing in a fluid medium, in each of said N different reaction vessels, reagents for performing a binding assay and wherein said reagents are the same for all said N different reaction vessels, one of said reagents being a second component of said binding pair and wherein said second component carries a signal moiety, under conditions such that a portion of the amount of said second component carrying said signal moiety is caused to be bound to said first component during said assay, in each one of said N different reaction vessels; and
   e) combining the contents of said N different reaction vessels to form a mixture, and
   f) analyzing the mixture by flow cytometry wherein
      i) measurement of said signal moiety indicates at least one of the following:
         presence or absence of said compound to be tested, concentration of said compound to be tested, and biological activity of said compound to be tested; and
      ii) measurement of said detectable label indicates the sample containing said compound to be tested.

2. The method of claim 1, wherein N is 80–100,000.
3. The method of claim 1, wherein N is from 80 to 4000.
4. The method of claim 1, wherein said reactant bound to said carrier beads is pre-coated on said carrier beads.
5. The method of claim 1, wherein said detectable label comprises at least one fluorescent dye.
6. The method of claim 1, wherein said detectable label comprises an electronic label.
7. The method of claim 1, wherein said signal moiety is a fluorescent dye.
8. A method for assaying N samples, wherein N is greater than or equal to 2, said samples each containing a single compound to be tested, said method comprising:
   a) providing N populations of carrier beads wherein the carrier beads of each population comprise a detectable label for distinguishing the carrier beads of each population from the carrier beads of every other population, and a reagent bound thereto, said reagent being the same for said carrier beads in all of said N populations;
   b) dispensing one distinguishable population of said N populations of carrier beads into a separate, corresponding one of N different reaction vessels, so that said one of N different reaction vessels contains one of said N populations, and performing said dispensing for each population of said N populations;
   c) dispensing one of said N samples having a single compound to he tested, into a separate, corresponding one of said N different reaction vessels so that said one of N different reaction vessels contains one of said N samples and one of said N populations, and performing said dispensing for each sample of said N samples;
   d) combining in a fluid medium, in each of said N different reaction vessels additional reagents for performing an assay wherein said additional reagents are the same for all said N reaction vessels, and wherein one of said additional reagents or said reagent bound to said carrier bead carries a signal moiety, under conditions such that a portion of said signal moiety is caused to be partitioned between said carrier beads and said fluid medium during said assay, in each one of said N different reaction vessels;
   e) combining the contents of said N different reaction vessels to form a mixture, and
   f) analyzing the mixture by flow cytometry; wherein
      i) measurement of said signal moiety indicates at least one of the following:
         presence or absence of said compound to be tested, concentration of said compound to be tested, and biological activity of said compound to be tested; and
      ii) measurement of said detectable label indicates the sample containing said compound to be tested.

9. The method of claim 8, wherein N is 80–100,000.
10. The method of claim 8, wherein N is from 80 to 4000.
11. The method of claim 8, wherein said reagent, bound to said carrier beads is pre-coated on said carrier beads.
12. The method of claim 8, wherein said detectable label comprises at least one fluorescent dye.
13. The method of claim 8, wherein said detectable label comprises an electronic label.
14. The method of claim 8, wherein said signal moiety is a fluorescent dye.

* * * * *